United States Patent
Marchionni et al.

(10) Patent No.: US 6,872,698 B2
(45) Date of Patent: Mar. 29, 2005

(54) METHODS FOR TREATING NEUROLOGICAL INJURIES AND DISORDERS

(75) Inventors: Mark Marchionni, Arlington, MA (US); Michael Jarpe, Marlborough, MA (US); Ted Ebendal, Uppsala (SE)

(73) Assignee: Scion Pharmaceuticals, Inc., Medford, MA (US)

(*) Notice: Subject to any disclaimer, the term of this patent is extended or adjusted under 35 U.S.C. 154(b) by 0 days.

(21) Appl. No.: 09/756,481

(22) Filed: Jan. 8, 2001

(65) Prior Publication Data

US 2003/0069176 A1 Apr. 10, 2003

Related U.S. Application Data

(63) Continuation of application No. PCT/US99/15106, filed on Jul. 2, 1999.
(60) Provisional application No. 60/091,791, filed on Jul. 6, 1998.

(51) Int. Cl.[7] ................................................ A61K 38/18
(52) U.S. Cl. ............................................. 514/2; 514/12
(58) Field of Search ........................................ 514/2, 12

(56) References Cited

U.S. PATENT DOCUMENTS

| 5,635,372 A | 6/1997 | Celeste et al. |
| 5,652,118 A | 7/1997 | Ozkaynak et al. |
| 5,767,252 A | 6/1998 | Worley et al. |

FOREIGN PATENT DOCUMENTS

| WO | WO 92/00382 | * 1/1992 |

OTHER PUBLICATIONS

Rudinger, In *Peptide Hormones*, Q. A. Parsons, ed. University Park Press, Baltimore, pp. 1–7, 1976.*
L. Farkas et al., *Neuroscience Letters*, 236:120–122 (1997).

* cited by examiner

*Primary Examiner*—Brenda Brumback
*Assistant Examiner*—Stephen Gucker
(74) *Attorney, Agent, or Firm*—Jeffrey D. Hsi; Christine C. O'Day; Edwards & Angell, LLP

(57) ABSTRACT

The present invention relates to methods for treatment of nerve cell death (degeneration) and neurodegenerative diseases. Methods of the invention include administering, an effective amount of GDF-1 alone or in combination with neurotrophin-3, to a patient in need of such treatment such as a person suffering from stroke or traumatic brain injury or a neurodegenerative disease.

5 Claims, 3 Drawing Sheets

FIG. 1

|   |   |
|---|---|
| FIG. 1A | |
| FIG. 1B | FIG. 1 |
| FIG. 1C | |

FIG. 1A

```
1    CCCTTCTCCAGGGACTCTGGCTGCCAGCAGCTCCGCCCTTTCAGATCAATTCTCGACCACC    60
61   CACCTTGGGACTGCCGCCCAGTCCCTGCCCTCGCCCTGGATCAGTGGGGTCCAGACGCCCCCT   120
121  CCAGGACCTCAAAGCACCCCCGACCTAAGGTCACCAGCCGCCCACTGCCCAGAGCGCAGTGG   180
181  GCTCCGCTGACTCTCTTGACACCTCCTGGGAGGAAAATGCTCCCTGTCTGCCATCGTTT      240
                                  M  L  P  V  C  H  R  P
241  TTGCGACCACCTCCTCCTCCTGCTCTTGCCCTCGACGACCCTGGCCCCGCGCCAGC        300
      C  A  H  L  L  L  L  L  P  S  T  T  L  A  P  A  P  A
301  ATCCATGGGCCCCGCTGCCGCCGCCCTGCTCGGCGTTCTCGGCTTCTTGGGCTTGCCCGAG    360
      S  M  G  P  A  A  A  A  L  L  G  V  L  G  L  P  E  A  P  R  S
361  CGTCCCCACACACCGACCTGTGCCTCCTGTCATGTGGCGCCTATTCCGTCGCCGTGACCC    420
      V  P  T  H  R  P  P  V  M  W  R  L  P  A  A  A  A  P
421  CCAGGAGGCCAGAGTGGGGACGGCCCCTCTGCGGCCATGCCACGTGGAGGAACTAGGGGTCGC   480
      Q  E  A  R  V  G  R  P  L  R  P  C  H  V  E  E  L  G  V  A
481  CGGAAACATTGTGCGCCACATCCCCGACAGCGGTCTGTCCTCCAGGCCCGCACAACCCGC     540
      G  N  I  V  R  H  I  P  D  S  G  L  S  S  R  P  A  Q  P  A
```

```
541  CAGGACCTCGGGGCTGTGCCCCGAGTGGACAGTCGTCTTTGACCTGTCGAATGTGGAGCC    600
      R  T  S  G  L  C  P  E  W  T  V  V  F  D  L  S  N  V  E  P

601  CACAGAGCGCCAACACGCGGCGCTTAGACTTGCGGCTGAGGCTGAGTGTGAAGATAC       660
      T  E  R  P  T  R  A  R  L  E  L  R  L  E  A  E  C  E  D  T

661  AGGAGGGTGGGAGCTAAGCCACTGTGGCCGACGCAGAGCATCCAGGCTGAGCT           720
      G  G  W  E  L  S  V  A  L  W  A  D  A  E  H  P  G  P  E  L

721  GCTGCGCGTGCCGGCCACCAGGGGTGCTCCTGCGCGCAGACCTACTGGGACTGCAGT       780
      L  R  V  P  A  P  P  G  V  L  L  R  A  D  L  L  G  T  A  V

781  AGCCGCCAACGCCATCAGTGCCCTGTACTGTGCGCTGTCACTGCACCCTGGGGC          840
      A  A  N  A  S  V  P  C  T  V  R  L  A  L  S  L  H  P  G  A

841  CACTGCAGCCTGTGGGCGCTGAGGCCTCCCTGCTGGTGACGCTGGACCCCACG           900
      T  A  C  G  R  L  A  E  A  S  L  L  V  T  L  D  P  R

901  CCTGTGTCCCCTTGCCGCGATTGCGCGCCACACGGAGCCCAGGGTAGAAGTTGGTCCAGT    960
      L  C  P  L  P  R  L  R  R  H  T  E  P  R  V  E  V  G  P  V
```

FIG. 1B

```
 961  GGGCACTTGTCGTACCCGACGGTTGCATGTGAGCTTCCGTGAGGTGGGCTGGCACCGTTG  1020
       G  T   C  R  T  R  R  L  H  V  S  F  R  E  V  G  W  H  R  W

1021  GGTGATCGCGCCGCGGTGGCCTTCCTAGCCAACTTCTGCCAGGGCACGTGCGCACTACCCGA  1080
       V  I  A  P  R  G  F  L  A  N  F  C  Q  G  T  C  A  L  P  E

1081  AACGCTGAGGGGACCCGGCGGCCTGCACTCAACCACGCTGTGCTGCGCGCGCTCAT  1140
       T  L  R  G  P  G  G  P  P  A  L  N  H  A  V  L  R  A  L  M

1141  GCACGCAGCTGCTCCCACCCCGGCTGCTGCCAGGCTGCTGCCAGAGCGTCTATC  1200
       H  A  A  P  T  P  G  A  G  S  P  C  C  V  P  E  R  L  S

1201  ACCCATCTCCGTGCTCTTCTTCGACAATAGTGACAACGTGGTCCTGCGACACTACGAAGA  1260
       P  I  S  V  L  F  F  D  N  S  D  N  V  V  L  R  H  Y  E  D

1261  CATGGTGGTGGATGAGTGTGGCTGCCGTTGACCACCCGGGACACCCTTTCAGGGACCGCC  1320
       M  V  D  E  C  G  C  R

1321  CCACGCAAAAGCAGGGACTGTTTGTTCATGTTTTATTGGTGACAAAAGCTTAAAACAAA  1380

1381  TTTGACT  1387
```

METHODS FOR TREATING NEUROLOGICAL INJURIES AND DISORDERS

The present application is a continuation of PCT/US99/15106, filed Jul. 2, 1999, which claims the benefit of U.S. provisional application No. 60/091,791, filed Jul. 6, 1998, which is incorporated herein by reference in its entirety.

BACKGROUND OF THE INVENTION

1. Field of the Invention

The present invention relates to methods for treatment of neurological injuries and neurodegenerative disorders. More particularly, in one aspect, the invention includes methods of use of the polypeptide GDF-1, or a fragment or derivative of GDF-1, or a nucleic acid encoding GDF-1, to treat a subject suffering from or susceptible to a neurological injury or neurodegenerative disease. The invention also provides methods for treatment of neurological injury and neurodegenerative disease with a combination of GDF-1 that comprise administration of a combination of GDF-1 and neurotrophin-3 (NT-3).

2. Background

Nerve cell death (degeneration) can cause potentially devastating and irreversible effects for an individual and may occur e.g. as a result of stroke, heart attack or other brain or spinal chord ischemia or trauma. Additionally, neurodegenerative disorders, such as Alzheimer's disease, Parkinson's disease, Huntington's disease, Amyotrophic Lateral Sclerosis, Down's Syndrome and Korsakoff's disease, involve nerve cell death (degeneration).

Therapies have been investigated to treat nerve cell degeneration and related disorders, e.g., by limiting the extent of nerve cell death that may otherwise occur to an individual as well as promoting repair, remodeling and reprogramming after stroke or other neuronal injury. See, e.g., F. Seil, *Curr Opin Neuro*, 10:49–51 (1997); N. L. Reddy et al., *J Med Chem*, 37:260–267 (1994); and WO 95/20950.

Certain growth factors have been reported to exhibit neuroprotective properties. In particular, nerve growth factor (NGF) has been evaluated in certain animal models of injury to or degeneration of nervous tissue. See, for example, G. Sinson et al., *J. Neurosurg*, 86(3):511–518 (1997); and G. Sinson et al., *J Neurochem*, 65(5):2209–2216 (1995). Osteogenic protein-1 (OP-1) has been evaluated in a rat model of cerebral hypoxia/ischemia for neuroprotective activity. G. Perides, *Neurosci Lett*, 1871):21–24 (1995). Glial cell line-derived neurotrophic factor (GDNF) was reported to exhibit trophic activity on certain populations of central neurons. Y. Wang et al., *J Neurosci*, 17(11):4341–4348 (1997). Small molecules, such as MK-801, also have been investigated as neuroprotective agents. See B. Meldrum, *Cereb Brain Metab Rev*, 2:27–57 (1990); D. Choi, *Cereb Brain Metab Rev*, 2:27–57 (1990).

However, no effective pharnacotherapies are in regular clinical use for ischemia-induced brain injury or other such injuries and disorders. See, for example, Y. Wang et al., supra; G. Sinson et al., *J Neurochem*, 65(5):2209 (1995).

It thus would be highly desirable to have new neuroprotective agents, particularly agents to limit the extent or otherwise treat nerve cell death (degeneration) that occur with stroke, heart attack or brain or spinal cord trauma, or to treat Alzheimer's disease, Parkinson's disease, Huntington's disease, Amyotrophic Lateral Sclerosis, Down's Syndrome and Korsakoffs disease. It also would be desirable to have agents that promote repair, remodeling or reprogramming after stroke or other neuronal injury.

SUMMARY OF THE INVENTION

The present invention provides methods for treatment and prophylaxis of nerve cell death (degeneration) and neurodegenerative disease. The methods of the invention can provide enhanced neurotrophin activity in both the central and peripheral nervous system and e.g. promote increased neuron survival and neurite outgrowth.

Therapies of the invention are particularly effective for the treatment or prophylaxis of the effects of stroke, brain or spinal cord injury or ischemia, heart attack, optic nerve and retinal injury and ischemia and other acute-type conditions disclosed herein as well as chronic-type neurodegenerative conditions, such as epilepsy, Alzheimer's disease, Parkinson's disease, Huntington's disease, Amyotrophic Lateral Sclerosis, Down's Syndrome, Korsakoff's disease, cerebral palsy and/or age-dependent dementia.

Methods of the invention also include therapies for promoting repair, remodeling or reprogramming after stroke or other neuronal injury, neurodegenerative disease or neuropathy.

Methods of the invention further include treatments to improve the functional capability of a mammal that has suffered from stroke or other neuronal injury, neurodegenerative disease or neuropathy, e.g. to improve motor function as well as cognitive abilities.

The invention further provides methods for treatment of peripheral nerve damage.

Therapeutic methods of the invention include administration of GDF-1, or a fragment or derivative of GDF-1, or a nucleic acid encoding GDF-1 or a GDF-1 fragment or derivative, to a patient in the need thereof, such as a subject that is suffering from, has suffered or is susceptible to nerve cell death or a neurodegenerative disease or neuropathy. GDF-1 has the nucleotide and amino acid sequence set forth in FIG. 1 (SEQ ID NOS. 1–2).

The invention further provides therapeutic methods that comprise administration of GDF-1, or fragment or derivative of GDF-1, or a nucleic acid encoding GDF-1 or a GDF-1 fragment or derivative, in combination with neurotrophin-3 (NT-3) or a nucleic acid encoding NT-3, to a patient in the need thereof, such as a subject that is suffering from, has suffered or is susceptible to nerve cell death or a neurodegenerative disease.

Surprisingly, it has been found that significantly enhanced neuroprotective and neuronal cell growth effects are provided by the combined use of GDF-1 and NT-3 in accordance with the invention. See, for instance, the results set forth in Example 4 which follows.

Typical patients that may be treated in accordance with the methods of the invention are persons suffering from or susceptible to neuropathies, e.g. brain or spinal cord trauma or ischemia, stroke, heart attack, hypoxia, hypoglycemia, post-surgical neurological deficits, decreased blood flow or nutrient supply to retinal tissue or optic nerve, retinal trauma or ischemia, optic nerve injury or glaucoma.

The methods of the invention are especially useful to treat a person susceptible or suffering from stroke or heart attack or neurological deficits relating to cardiac arrest, a person suffering or susceptible to brain or spinal cord injury, a person suffering from the effects of retinal ischemia or degeneration, or a person suffering from decreased blood flow or nutrient supply to retinal tissue or optic nerve or retinal trauma or optic nerve injury.

Patients suffering from a neurodegenerative disease also may be treated in accordance with the methods of the invention, including patients suffering from epilepsy, Parkinson's disease, Huntington's disease, Amyotrophic Lateral Sclerosis, Alzheimer's disease, Down's Syndrome, Korsakoff's disease, cerebral palsy and/or age-dependent dementia.

Also, the methods of the invention include treatment to promote repair, remodeling or reprogramming to a subject that has suffered stroke or other neuronal injury such as traumatic brain or spinal cord injury. In such cases, the therapeutic agent(s) may be suitably administered to the subject over an extended period following the injury, e.g. at least about 1, 2, 3, 4, 6, 8, 12 or 16 weeks following the injury.

Other aspects of the invention are disclosed infra.

BRIEF DESCRIPTION OF THE DRAWINGS

FIG. 1 shows a nucleotide sequence (that nucleotide sequence often referred to herein as SEQ ID NO: 1) of DNA encoding GDF-1 and the amino acid sequence (that amino acid sequence often referred to herein as SEQ ID NO:2) of GDF-1. The poly A tail is not shown. Numbers indicate nucleotide position relative to the 5' end of the clone.

DETAILED DESCRIPTION OF THE INVENTION

As stated above, the invention includes methods for treatment and/or prophylaxis of nerve cell death (degeneration) and neurodegenerative disease that comprise administration of an effective amount of a GDF-1 or a fragment of derivative of GDF-1, or a nucleic acid that encodes GDF-1 or a fragment or derivative of GDF-1.

A "fragment" or "derivative" of GDF-1 refers to herein 1) a peptide in which one or more amino acid residues are substituted with a conserved or non-conserved amino acid residue (preferably a conserved amino acid residue) and such substituted amino acid residue may or may not be one encoded by the genetic code, or (ii) a peptide in which one or more of the amino acid residues includes a substituent group, or (iii) a peptide in which the mature protein is fused with another compound, such as a compound to increase the half-life of the polypeptide (for example, polyethylene glycol). Thus, a fragment or derivative for use in accordance with the methods of the invention includes a proprotein, which can be activated by cleavage of the proprotein portion to produce an active mature polypeptide. Moreover, GDF-1 has potential N-linked glycosylation sites. Such glycosyl groups can be partially or completely removed or otherwise modified to provide a GDF-1 derivative or fragment.

The GDF-1 fragments and derivatives of the invention are of a sufficient length to uniquely identify a region of GDF-1. GDF-1 fragments thus preferably comprise at least 8 amino acids, usually at least about 12 amino acids, more usually at least about 15 amino acids, still more typically at least about 30 amino acids, even more typically at least about 50 or 70 amino acids. Preferred fragments or derivatives for use in the methods of the invention include those that have at least about 70 percent homology (sequence identity) to SEQ ID NO:2 (amino acid sequence shown in FIG. 1 of the drawings), more preferably about 80 percent or more homology to SEQ ID NO:2, still more preferably about 85 to 90 percent or more homology to SEQ ID NO:2. Sequence identity or homology with respect to GDF-1 refers to herein as the percentage of amino acid sequences of a GDF-1 protein or fragment or derivative thereof that are identical with SEQ ID NO:2, after introducing any gaps necessary to achieve the maximum percent homology.

The GDF-1 fragments and derivatives for use in the methods of the invention preferably exhibit good activity in standard neuroprotective assays such as the in vivo cerebral ischemia assay of Example 1, which follows. That assay includes the following steps: a) continuous intraventricular infusion of the protein fragment or derivative or vehicle alone to test rats for three days prior to inducing focal ischemic infarcts in right lateral cerebral cortex; and b) twenty-four hours after inducing ischemic infarcts, infarct volume in each test animal is determined by image analysis. Preferably, a protein fragment or derivative of the invention provides at least about a 10% reduction in infarct volume relative to vehicle-treated animals, more preferably about a 20% reduction in infarct volume, still more preferably about a 25% reduction in infarct volume relative to vehicle-treated animals in such an assay. References herein to in vivo cerebral ischemia assay are intended to refer to an assay of the above steps a) and b), which are more fully described in Example 1 which follows.

As discussed above, GDF-1 nucleic acid fragments and derivatives are also provided for use in the methods of the invention. Those fragments and derivatives typically are of a length sufficient to bind to the sequence of SEQ ID NO:1 under the following moderately stringent conditions (referred to herein as "normal stringency" conditions): use of a hybridization buffer comprising 20% formamide in 0.8M saline/0.08M sodium citrate (SSC) buffer at a temperature of 37° C. and remaining bound when subject to washing once with that SSC buffer at 37° C.

Preferred GDF-1 nucleic acid fragments and derivatives of the invention will bind to the sequence of SEQ ID NO:1 under the following highly stringent conditions (referred to herein as "high stringency" conditions): use of a hybridization buffer comprising 30% formamide in 0.9M saline/0.09M sodium citrate (SSC) buffer at a temperature of 45° C. and remaining bound when subject to washing twice with that SSC buffer at 45° C.

The GDF-1 nucleic acid fragments and derivatives preferably should comprise at least 20 base pairs, more preferably at least about 50 base pairs, and still more preferably a nucleic acid fragment or derivative of the invention comprises at least about 100, 200, 300 or 400 base pairs. In some preferred embodiments, the nucleic acid fragment or derivative is bound to some moiety which permits ready identification such as a radionucleolide, fluorescent or other chemical identifier.

Particularly preferred GDF-1 fragments and derivatives of the invention have substantial homology (sequence identity) to SEQ ID NO:1 (nucleic acid sequence shown in FIG. 1 of the drawings), preferably at least about 70 percent homology (sequence identity) to SEQ ID NO:1, more preferably about 80 percent or more homology to SEQ ID NO:1, still more preferably at least about 85, 90 or 95 percent homology to SEQ ID NO:1. Sequence identity or homology with respect to the nucleic acid sequence of GDF-1 shown in FIG. 1 of the drawings refers to herein as the percentage of base sequences of a GDF-1 nucleic acid fragment or derivative thereof that are identical with SEQ ID NO:1, after introducing any gaps necessary to achieve the maximum percent homology.

Isolated GDF-1 and peptide fragments or derivatives of the invention are preferably produced by recombinant methods. See the procedures disclosed in Example 3, which follows. A wide variety of molecular and biochemical methods are available for generating and expressing GDF-1; see e.g. the procedures disclosed in *Molecular Cloning, A Laboratory Manual* (2nd Ed., Sambrook, Fritsch and Maniatis, Cold Spring Harbor), *Current Protocols in Molecular Biology* (Eds. Aufubel, Brent, Kingston, More, Feidman, Smith and Stuhl, Greene Publ. Assoc., Wiley-Interscience, NY, N.Y. 1992) or other procedures that are otherwise known in the art. For example, GDF-1 or fragments or derivatives thereof may be obtained by chemical synthesis, or more preferably by expression in bacteria such as *E. coli* and eukaryotes such as yeast, baculovirus, or mammalian cell-based expression systems, etc., or alternatively produced by a transgenic animal, depending on the size, nature and quantity of GDF-1 or fragment or derivative thereof. More particularly, a recombinant DNA molecule comprising a vector and a DNA segment encoding GDF-1, or a fragment or derivative thereof, can be constructed. Suitable vectors include e.g. baculovirus-derived vectors for expression in insect cells (see Pennock et al., *Mol. Cell. Biol.*, 4:399–406 (1984)), T7-based expression vector for expression in bacteria (see Rosenberg et al., *Gene*, 56:125–135 (1987)) and the pMSXND expression vector for expression in mammalian cells (Lee and Nathans, *J. Biol. Chem.*, 263:3521–3527 (1988)). The DNA segment can be present in the vector operably linked to regulatory elements, e.g., a promoter (e.g., polyhedrin, T7 or metallothionein (Mt-I) promoters), or a leader sequence to provide for secretory expression of the polypeptide. The recombinant DNA molecule containing the DNA coding for GDF-1 or a fragment or derivative thereof can be introduced into appropriate host cells by known methods. Suitable host cells include e.g. prokaryotes such as *E. coli*, Bacillus subtillus, etc., and eukaryotes such as animal cells and yeast strains, e.g., *S. cerevisiae*. Mammalian cells may be preferred such as J558, NSO, SP2-O or CHO. In general, conventional culturing conditions can be employed. See Sambrook, supra. Stable transformed or transfected cell lines can then be selected. The expressed GDF-1 or fragment or derivative thereof then can be isolated and purified by known methods. Typically the culture medium is centrifuged and the supernatant purified by affinity or immunoaffinity chromatography, e.g. Protein-A or Protein-G affinity chromatography or an immunoaffinity protocol comprising use of monoclonal antibodies that bind GDF-1.

GDF-1 nucleic acids used in the methods of the invention are typically isolated, meaning the nucleic acids comprise a sequence joined to a nucleotide other than that which it is joined to on a natural chromosome and usually constitute at least about 0.5%, preferably at least about 2%, and more preferably at least about 5% by weight of total nucleic acid present in a given fraction. A partially pure nucleic acid constitutes at least about 10%, preferably at least about 30%, and more preferably at least about 60% by weight of total nucleic acid present in a given fraction. A pure nucleic acid constitutes at least about 80%, preferably at least about 90%, and more preferably at least about 95% by weight of total nucleic acid present in a given fraction.

As discussed above, it has been found that significantly enhanced neuroprotective and neuronal cell growth effects can result from the combined use of GDF-1 and neurotrophin-3 (NT-3). NT-3 can be obtained commercially (e.g. Pepro Tech Inc.; Rocky Hill, N.H., or other sources), and the nucleic acid and amino acid sequences of neurotrophin-3 (NT-3) are known. See EP7042192, EP0441947 and WO 91/03569.

In the combination therapy, GDF-1 and NT-3 may be administered simultaneously, in the same or different pharmaceutical formulations, or sequentially. However, if administered sequentially, GDF-1 and NT-3 are preferably administered within a sufficient time to achieve the desired pharmacological effects of enhanced neuroprotective and neuronal cell growth effects.

As discussed above, the NT-3 protein or nucleic acid encoding NT-3 may be administered to a patient. It is generally more preferred that the NT-3 polypeptide is administered to a patient. Nucleic acid coding for NT-3 preferably is at least partially pure, i.e. the NT-3 nucleic acid constitutes at least about 10%, preferably at least about 30%, and more preferably at least about 60% by weight of nucleic acid present in a given fraction. More typically the NT-3 nucleic acid will be substantially pure, i.e. the nucleic acid constitutes at least about 80%, more preferably at least about 90%, and more preferably at least about 95% by weight of total nucleic acid in a given fraction.

As discussed above, the methods of the invention include treating and preventing neurological disorders, including the consequences of stroke, heart attack, traumatic head or brain injury, spinal cord injury, epilepsy or neurodegenerative diseases comprising the administration of an effective amount of GDF-1 or fragment or derivative thereof, or nucleic acid encoding same, optionally with co-administration of NT-3 or nucleic acid encoding NT-3, to a subject including a mammal, particularly a human, in need of such treatment.

In particular, the invention provides methods for treatment and/or prophylaxis of nerve cell death (degeneration) resulting e.g. from hypoxia, hypoglycemia, brain or spinal cord ischemia, brain or spinal cord trauma, stroke, heart attack or drowning. Typical candidates for treatment include e.g. heart attack, stroke and/or persons suffering from cardiac arrest, neurological deficits, brain or spinal cord injury patients, patients undergoing major surgery such as heart surgery where brain ischemia is a potential complication and patients such as divers suffering from decompression sickness due to gas emboli in the blood stream. Candidates for treatment also will include those patients undergoing a surgical procedure involving extra-corporal circulation such as e.g. a bypass procedure.

The invention also provides methods for treatment which comprise administration of GDF-1 or fragment or derivative thereof, or nucleic acid encoding same, optionally with co-administration of NT-3 or nucleic acid encoding NT-3, to a patient that is undergoing surgery or other procedures where brain or spinal cord ischemia or injury is a potential risk. For example, carotid endarterectomy is a surgical procedure employed to correct atherosclerosis of the carotid arteries. Major risks associated with the procedure include intraoperative embolization and the danger of hypertension in the brain following increased cerebral blood flow, which may result in aneurysm or hemorrhage. Thus, an effective amount of the therapeutic agent(s) could be administered pre-operatively, peri-operatively or post-operatively to reduce such risks associated with carotid endarterectomy, or other post-surgical neurological deficits.

The invention also is effective to promote and enhance recovery or function from acute nerve cell death and neurological conditions. Thus, for example, GDF-1 or fragment or derivative thereof, or nucleic acid encoding same, optionally with co-administration of NT-3 or nucleic acid encoding NT-3, could be administered to promote repair, remodeling or reprogramming to a patient that has suffered from stroke or other neuronal injury, suitably for an extended period as discussed above. A therapeutic agent(s) of the invention also could be administered post-operatively to promote recovery from any neurological deficits that may have occurred to a patient that has undergone surgery.

Behavioral outcome studies can be particularly useful to assess the efficacy of a particular GDF-1 or fragment or derivative thereof, or nucleic acid encoding same, to promote such recovery, repair and remodeling from acute nerve cell death and/or neurological conditions. Suitable behavioral assays are disclosed in Example 2, which follows. For additional suitable assays, see J. Aronowksi et al., *J Cereb Blood Flow Metab*, 16:705–713 (1996); G. Sinson et al., *J Neurochem*, 65(5):2209–2214 (1995); T. K. McIntosh et al., Neuroscience, 28:233–244 (1989); and T. K. McIntosh et al., *J Neurotrauma*, 10:373–384 (1993).

The invention further includes methods for prophylaxis against neurological deficits resulting from e.g. coronary artery bypass graft surgery and aortic valve replacement surgery, or other procedure involving extra-corporal circulation. Those methods will comprise administering to a patient undergoing such surgical procedures an effective amount of GDF-1 or fragment or derivative thereof, or nucleic acid encoding same, optionally with co-administration of NT-3 or nucleic acid encoding NT-3. Suitably administration will be pre-operatively, peri-operatively or post-operatively.

The invention also provides methods for prophylaxis and treatment against neurological injury for patients undergoing myocardial infarction, a procedure that can result in ischemic insult to the patient. Such methods will comprise administering to a patient undergoing such surgical procedure an effective amount of GDF-1 or fragment or derivative thereof, or nucleic acid encoding same, optionally with co-administration of NT-3 or nucleic acid encoding NT-3. Typically administration will be either pre-operatively or peri-operatively.

The invention also provides methods for treatment or prevention of peripheral nerve damage, comprising administering to a subject that is suffering from or susceptible to peripheral nerve damage an effective amount of GDF-1 or fragment or derivative thereof, or nucleic acid encoding same, optionally with co-administration of NT-3 or nucleic acid encoding NT-3.

Also provided are methods for treating or preventing neuropathic pain such as may be experienced by cancer patients, persons having diabetes, amputees and other persons who may experience neuropathic pain. These methods for treatment comprise administration of an effective amount of GDF-1 or fragment or derivative thereof, or nucleic acid encoding same, to a patient in need of such treatment.

The invention also provides methods for treatment and prophylaxis against retinal ischemia or degeneration and resulting visual loss. For example, GDF-1 or fragment or derivative thereof, optionally in combination with NT-3 or nucleic acid encoding NT-3, can be administered parenterally or by other procedures as described herein to a subject a suffering from or susceptible to ischemic insult that may adversely affect retinal function, e.g., significantly elevated intraocular pressures, diseases such as retinal artery or vein occlusion, diabetes or other ischemic ocular-related diseases. Post-ischemic administration also may limit retinal damage. The invention also includes methods for treatment of and prophylaxis against decreased blood flow or nutrient supply to retinal tissue or optic nerve, or treatment of or prophylaxis against retinal trauma or optic nerve injury. Subjects for treatment according to such therapeutic methods of the invention may be suffering from or susceptible to retinal ischemia that is associated with atherosclerosis, venous capillary insufficiency, obstructive arterial or venous retinopathies, senile macular degeneration, cystoid macular edema or glaucoma, or the retinal ischemia may be associated with a tumor or injury to the mammal. Intravitreal injection also may be a preferred administration route to provide more direct treatment to the ischemic retina.

The invention further provides a method of treating Korsakoff's disease, a chronic alcoholism-induced condition, comprising administering to a subject including a mammal, particularly a human, an effective amount of GDF-1 or fragment or derivative thereof, in an amount effective to treat the disease. Compounds of the invention are anticipated to have utility for the attenuation of cell loss, hemorrhages and/or amino acid changes associated with Korsakoff's disease.

The invention further includes methods for treating a person suffering from or susceptible to epilepsy, emesis, narcotic withdrawal symptoms and age-dependent dementia, comprising administering to a subject including a mammal, particularly a human, an effective amount of GDF-1 or fragment or derivative thereof, in an amount effective to treat the condition.

It will be appreciated that in some instances that a polypeptide (i.e. GDF-1 or a fragment or derivative thereof or NT-3) will be preferably administered to a subject rather than nucleic acid, particularly where a patient is suffering from or susceptible to an acute neurological injury that demands immediate therapy. For example, administration of a polypeptide may be preferred to a patient suffering from stroke, heart attack, traumatic brain injury and the like where it is desired to deliver the active therapeutic as quickly as possible.

In the therapeutic methods of the invention, NT-3 and GDF-1 peptides and nucleic acids may be suitably administered to a subject such as a mammal, particularly a human, by any of a number of routes including parenteral (including subcutaneous, intramuscular, intravenous and intradermal), oral (including inhalation), rectal, nasal, vaginal and topical (including buccal and sublingual) administration. NT-3 and GDF-1 protein or nucleic acid or a fragment or derivative thereof may be administered to a subject alone or as part of a pharmaceutical composition, comprising the peptide or nucleic acid together with one or more acceptable carriers and optionally other therapeutic ingredients. The carriers should be "acceptable" in the sense of being compatible with the other ingredients of the formulation and not deleterious to the recipient thereof.

GDF-1 protein or nucleic acid or a fragment or derivative thereof, and optionally NT-3 or nucleic acid, may be administered to a subject as the sole active pharmaceutical agent(s) or those agent(s) can be used in combination with other therapeutic agents, e.g. OP-1 or small molecule therapeutics, or other compounds.

Nucleic acids encoding GDF-1 or a GDF-1 fragment or derivative or NT-3 can be administered to a patient by generally known procedures. For example, the nucleic acids may be introduced into target cells by any method which will result in the uptake and expression of the nucleic acid by the target cells. These methods can include vectors, liposomes, naked DNA, adjuvant-assisted DNA, catheters, etc. Preferably the administered nucleic acid codes for an appropriate secretory sequence to promote expression upon administration. Suitable vectors for administering a nucleic acid in accordance with the invention include chemical conjugates such as described in WO 93/04701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpes virus vectors such as a herpes simplex I virus (HSV) vector [A. I. Geller et al., *J. Neurochem*, 64:487 (1995); F. Lim et al., in *DNA Cloning: Mammalian Systems*, D. Glover, Ed. (Oxford Univ. Press, Oxford England) (1995); A. I. Geller et al., *Proc Natl. Acad. Sci.: U.S.A.*:90 7603 (1993); A. I. Geller et al., *Proc Natl. Acad. Sci USA*: 87:1149 (1990)], Adenovirus Vectors [LeGal LaSalle et al., *Science*, 259:988 (1993); Davidson, et al., *Nat. Genet.*, 3:219 (1993); Yang et al., *J. Virol.*, 69: 2004 (1995)] and Adeno-associated Virus Vectors [Kaplitt, M. G., et al., *Nat. Genet.*, 8:148 (1994)].

Pox viral vectors introduce the gene into the cell cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the specific condition being treated. The introduction can be by standard techniques, e.g. infection, transfection, transduction or transformation. Examples of modes of gene transfer include e.g., naked DNA, $Ca_3(PO_4)_2$ precipitation, DEAE dextran, electroporation, protoplast fusion, lipofecton, cell microinjection, and viral vectors.

A vector can be employed to target essentially any desired target cell. For example, stereotaxic injection can be used to direct the vectors (e.g. adenovirus, HSV) to a desired location. Additionally, the particles can be delivered by intracerebroventricular (icv) infusion using a minipump infusion system, such as a SynchroMed Infusion System. A method based on bulk flow, termed convection, has also proven effective at delivering large molecules to extended areas of the brain and may be useful in delivering the vector to the target cell (Bobo et al., *Proc. Natl. Acad. Sci. USA*, 91:2076–2080 (1994); Morrison et al., *Am. J Physiol.*, 266:292–305 (1994)). Other methods that can be used include catheters, intravenous, parenteral, intraperitoneal and subcutaneous injection, and oral or other known routes of administration.

Parenteral formulations may be in the form of liquid solutions or suspensions; for oral administration, formulations may be in the form of tablets or capsules; and for intranasal formulations, in the form of powders, nasal drops, or aerosols.

Methods well known in the art for making formulations are found in, for example, "Remington's Pharmaceutical Sciences." Formulations for parenteral administration may, for example, contain as excipients sterile water or saline, polyalkylene glycols such as polyethylene glycol, oils of vegetable origin, or hydrogenated naphthalenes, biocompatible, biodegradable lactide polymer, or polyoxyethylene-polyoxypropylene copolymers may be used to control the release of the present factors. Other potentially useful parenteral delivery systems include ethylene-vinyl acetate copolymer particles, osmotic pumps, implantable infusion systems, and liposomes. Formulations for inhalation may contain as excipients, for example, lactose, or may be aqueous solutions containing, for example, polyoxyethylene-9-lauryl ether, glycocholate and deoxycholate, or may be oily solutions for administration in the form of nasal drops, or as a gel to be applied intranasally. Formulations for parenteral administration may also include glycocholate for buccal administration, methoxysalicylate for rectal administration, or citric acid for vaginal administration.

The concentration of NT-3 or GDF-1 or a fragment or derivative thereof, or nucleic acid encoding such polypeptides, administered to a particular subject will vary depending upon a number of issues, including the condition being treated, the mode and site of administration, the age, weight sex and general health of the subject, and other such factors that are recognized by those skilled in the art. Optimal administration rates for a given protocol of administration can be readily determined by those skilled in the art.

All documents mentioned herein are incorporated herein by reference. The invention is further illustrated by the following Examples. These Examples are provided to aid in the understanding of the invention and are not construed as a limitation thereof.

EXAMPLE 1

In vivo Neuroprotective Assay

GDF-1 and GDF-1 fragments and derivatives can be assessed for neuroprotective efficacy pursuant to the following assay.

Mature male Long-Evans rats (Charles River, 250–350 g) are allowed food and water ad libitum. Animals are anesthetized with sodium pentobarbital (60 mg/kg, i.p.) and placed in a stereotaxic head holder (David Kopf Instruments, Tujunga, Calif.). The dorsal surface of the skull is exposed by midline incision, and a small burr hole (2 mm diameter) is drilled over the right lateral ventricle, 1.6 mm lateral and 0.9 mm posterior to bregrna. A stainless steel cannula (I.D. 0.020", O.D. 0.028", 2 cm long) is then inserted stereotaxically into the ventricle to a depth of 4.4 mm beneath the surface of the skull. The tubing is suitably bent at a 90° angle 1–1.6 cm from its tip and connected to polyethylene tubing (I.D. 0.76 mm, O.D. 1.22 mm, 10 cm long) that is connected (by glue) to a mini-osmotic pump (Alzet 1007D, 100 $\mu$l fill volume, pump rate=0.5 $\mu$l/hr; Alza Corp., Palo Alto, Calif.) implanted subcutaneously in the back. The cannula can be suitably fixed to the skull by orthodontic resin (L. D. Culk Co., Milford, Del.) bonded to two small machine screws (⅛" stainless steel slotted) inserted in the skull. The pump, tubing, and cannula are primed before insertion with infusate solutions; a 3–0 nylon suture is inserted into the cannula during implantation to prevent obstruction by brain tissue. The wound is closed with 3-0 silk suture and cefazolin (10 mg, i.m.) is administered. After surgery animals are suitably kept in individual cages and fed soft food.

Pumps are filled with vehicle alone (containing 127 mM NaCl, 2.6 mM KCl, 1.2 mM $CaCl_2$, 0.9 mM $MgCl_2$, 4.14 mM HEPES, 3 mM glycerin, 0.001% bovine serum albumin [BSA], and 0.01% fast green), or vehicle GDF-1 or fragment or derivative thereof (100 $\mu$gm/ml). Heparin can be suitably used at relatively low doses, e.g. about 0.8 units/kg/day which is approximately 250–500 times less than a standard anticoagulant dose.

Three days after cannula implantation, animals are reanesthetized with 2% halothane and given atropine (0.15 mg/kg, i.p.). Animals are then intubated and connected to a ventilator (SAR-830; CWE Inc., Ardmore, Pa.) delivering 1% halothane/70% nitrous oxide in oxygen. The right femoral artery and vein are cannulated for monitoring of mean arterial blood pressure (MABP; Gould RS3200 Blood Pressure Monitor, Gould Inc., Valley View, Ohio), and blood sampling. Animals are then paralyzed with pancuronium bromide (0.5 mg/kg, i.v.). Arterial blood gasses (Coming 178 Blood Gas Analyzer, Ciba Coming Diagnostic Corp., Medford, Mass.), blood glucose (Accu-Check Blood Glucose Analyzer, Boehringer Mannheim, Indianapolis, Ind.), and hematocrit are measured at least twice during surgery and the immediate post-operative period. The stroke volume and rate of the ventilator are adjusted to maintain $PaO_2$ between 100–200 mm Hg and $PaCO_2$ between 30–40 mm Hg. Core body temperature may be monitored rectal thermocouple (e.g. Model 73ATA, Yellow Springs Instrument Co., Yellow Springs, Ohio) and maintained between 36–37° C. with a homeothermic blanket control unit (Harvard Bioscience, South Natick, Mass.).

Focal ischemic infarcts are made in the right lateral cerebral cortex in the territory of the middle cerebral artery (MCA) by the method of Chen, et al., *Stroke*, 17:738–743 (1986). Both common carotid arteries are exposed by midline anterior cervical incision. The animal is placed in a lateral position and a 1 cm skin incision was then made at the midpoint between the right lateral canthus and the anterior pinna. The temporal muscle is retracted, and a small (3 mm diameter) craniectomy is made at the junction of the zygoma and squamosal bone using a dental drill cooled with saline. Using a dissecting microscope, the dura can be opened with fine forceps, and the right MCA can be ligated with two 10-0 monofilament nylon ties just above the rhinal fissure and transected between the ties. Both common carotid arteries then can be occluded by microaneurysm clips for 45 minutes. After removal of the clips, return of flow is visualized in the arteries. Anesthesia is maintained for 15 minutes, and animals are returned to individual cages and fed soft food after surgery.

Twenty four hours after cerebral infarction, animals are again weighed, and then sacrificed by rapid decapitation. Brains are removed, inspected visually for the anatomy of the middle cerebral artery as well as for signs of hemorrhage or infection, immersed in cold saline for 10 minutes, and sectioned into six standard coronal slices (each 2 mm thick) using a rodent brain matrix slicer (Systems, Warren, Mich.). Brains are also examined visually for the presence of dye (fast green) in the cerebral ventricles. Slices are placed in. the vital dye 2,3,5-triphenyl tetrazolium chloride (TTC, 2%; Chemical Dynamics Co., NH) at 37° C. in the dark for 30 minutes, followed by 10% formalin at room temperature overnight. The outline of right and left cerebral hemispheres as well as that of infarcted tissue, clearly visualizable by lack of TTC staining (Chen et al., *Stroke*, 17:738–743 (1986)), is outlined on the posterior surface of each slice using an image analyzer (MTI videocamera and Sony video monitor connected to a Bioquant IV Image Analysis System run on an EVEREX computer). Infarct volume is calculated as the sum of infarcted area per slice multiplied by slice thickness. Both the surgeon and image analyzer operator are blinded to the treatment given each animal.

Volumes of infarcts among vehicle vs. GDF-1-treated animals can be compared by unpaired, two-tailed t-tests for each experiment, and by two-way analysis of variance (ANOVA; Exp. X Treatment) for combined data. A subsequent slice-by-slice analysis of infarct area among pooled GDF-1-vs. vehicle-treated animals is suitably done by repeated measures using a two-way ANOVA (Treatment X Slice). Other anatomical and physiological measurements are compared among GDF-1-vs. vehicle-treated animals by unpaired, two-tailed t-tests using the Bonferroni correction for multiple pairwise comparisons.

EXAMPLE 2
In vivo Behavioral Assays

For behavioral outcome studies, such as to assess recovery, repair and remodeling promoted by administration of GDF-1 or fragment or derivative thereof, or nucleic acid encoding same, a number of assays can be employed such as those described in J. Aronowksi et al., *J Cereb Blood Flow Metab*, 16:705–713 (1996); G. Sinson et al., *J Neurochem*, 65(5):2209–2214 (1995); T. K. McIntosh et al., *Neuroscience*, 28:233–244 (1989); and T. K. McIntosh et al., *J Neurotrauma*, 10:373–384 (1993).

Briefly, one suitable behavioral assay as described in G. Sinson et al., supra, entails that test animals (male Sprague-Dawley rats) receive preinjury training in a Morris Water Maze, a circular tank 1 m in diameter that is filled with 18° C. water. The water surface is made opaque with a covering of Styrofoam pieces. During training of the animals a submerged platform is present in the maze. Each test animal undergoes 20 training trials over a two day period during which they learn to locate the platform using external visual cues. Immediately following the last training trial, animals are anesthetized and subjected to a lateral (parasagittal) fluid-percussion (FP) brain injury. Briefly, a 5-mm carniectomy is performed over the left parietal cortex, midway between lamda and bregma. A hollow Leur-loc fitting is cemented to the craniectomy site. The injury is delivered after attaching the FP device. The injury should be of moderate severity (2.1–2.3 atm). After injury, the Leur-loc is removed, and the skin is sutured. Normothermia is maintained with warming pads until the animals being to ambulate.

At 72 hours, 1 week or 2 weeks after injury, animals are assessed for their ability to remember the learned task of locating the platform in the MWM. For this evaluation the platform is removed from the maze, and the animal's swimming pattern is suitably recorded with a computerized video system for 1 minute. The maze is separated in zones that are weighed according to the proximity to the platform's location. A memory score is generated by multiplying the weighted numbers by the time the animal spends in each zone and then adding the products.

Animals surviving for 1 or 2 weeks also can undergo evaluation of neurologic motor function. Briefly, one suitable assay provides that animals are scored from 0 (severely impaired) to 4 (normal) for each of the following: (1) left and (2) right forelimb during suspension by the tail; (3) left and (4) right hindlimb flexion when the forelimbs remain on a surface and the hindlimbs are lifted up and back by the tail; the ability to resist lateral pulsion to the (5) left and (6) right; and the ability to stand on an inclined plane in the (7) left, (8) right, and (9) vertical positions. Scores are combined for each of the steps (1) through (9). The observer for the tests should be blinded to the animal's previous treatment.

EXAMPLE 3
Cloning of GDF-1
Part 1. Construction and Screening of an 8.5 Day Embryonic cDNA Library.

All embryonic materials were obtained from random matings of CD-1 mice (Charles River). Mice were maintained according to the NIH guidelines for care and maintenance of experimental animals. The day on which the vaginal plug was noted was designated as day 0.5. Embryos were dissected out from the uterus, freed of all extraembryonic membranes, and frozen rapidly. Total RNA was prepared by homogenization in guanidinium thiocyanate buffer and centrifugation of the lysate through a cesium chloride cushion (Chirgwin et al., *Biochemistry*, 18:5294–5299 (1979)). Poly A-containing RNA was obtained by twice-selecting with oligo-dT cellulose (H. Aviv, *Proc. Natl. Acad. Sci. USA*, 69:1408–1412 (1972)). A cDNA library was constructed in the lambda ZAP II vector using the RNase H method (Okayama et al., *Mol. Cell Biol.*, 2:161–170 (1982)); and Gubler et al., *Gene*, 25:263–269 (1983)) according to instructions provided by Stratagene. Recombinant plaques (3.2 million) were obtained from 2 micrograms of starting RNA. The library was screened with the oligonucleotide 5'-GCAGCCACACTCCTCCACCACCATGTT-3' (SEQ ID NO:3) (corresponding to the amino acid sequence NMVVEECGC (SEQ ID NO:4)) which had been end-labeled using polynucleotide kinase. Hybridization was carried out in 6×SSC, 1× Denhardt's, 0.05% sodium pyrophosphate, 100 micrograms/ml yeast tRNA at 50° C. Filters were washed in 6×SSC, 0.05% sodium pyrophosate at 60° C.

Part 2: DNA Sequencing and Blot Hybridizations.

DNA sequencing of both strands was carried out with the dideoxy chain termination method (Sanger et al., *Proc. Natl. Acad. Sci., USA*, 74:5463–54-67 (1977)) using the exonuclease III/SI nuclease strategy (Henikoff, *Gene*, 28:351–359 (1984)).

For Northern analysis, RNA was electrophoresed on formaldehyde gels (Lehrach et al., *Biochemistry*, 16:4743–4751 (1977); and Goldberg, *Proc. Natl. Acad. Sci., USA*, 77:5794–5798 (1980)), transferred to nitrocellulose, and hybridized in 50% formamide, 5×SSC, 4×Denhardt's, 0.1% SDS, 0.1% sodium pyrophosphate, 100 µg/ml salmon DNA at 50° C. Filters were washed first in 2×SSC, 0.1% SDS, 0.1% sodium pyrophosphate, then in 0.1×SSC, 0.1% SDS at 50° C.

For Southern analysis, DNA was electrophoresed on 1% agarose gels, transferred to nitrocellulose, and hybridized in 1M NaCl, 50 mM sodium phosphate, pH 6.5, 2 mM EDTA, 0.5% SDS, 10×Denhardt's at 65° C. The final wash was carried out in 2×SSC at 68° C.

Part 3: In vitro Translation Experiments.

The full-length 1387 bp GDF-1 cDNA or a deletion mutant lacking the first 251 nucleotides was subcloned into the Bluescript vector (Stratagene), and sense or antisense RNA was transcribed in vitro from the T3 or T7 promoters (Golomb et al., *J. Virol.*, 21:743–752 (1977)); and McAllister et al., *Nucl. Acids Res.*, 8:4821–4837 (1980)) in the presence of cap analog, as described by Stratagene. In vitro translations were carried out by incubating 0.5 µg RNA, 17.5 µl rabbit reticulocyte lysate (Promega), and 20 µM cold amino acid mixture (Promega), and 20 µCi [$^{35}$S]methionine (New England Nuclear) in the presence or absence of 10 equivalents of dog pancreas microsomes (Promega) for 60 minutes at 30° C. Endoglycosidase digestions were carried out by diluting the translation reaction 1:30 with 100 mM sodium acetate pH 5.5, 0.1% SDS, 17 mU/ml endoglycosidase H (Boehringer-Mannheim). Protease digestions were carried out by diluting the translation reaction 1:20 with PBS, 1 mg/ml trypsin (Boehringer-Mannheim) in the presence or absence of 0.1% Triton X-100. All digestions were carried out for 3 hours at 37° C. Translation products were analyzed by electrophoresis on 10% SDS polyacrylamide gels (Laemmli, *Nature*, 227:680–685 (1970)) followed by fluorography with Enhance (New England Nuclear).

Part 4: Cloning and Nucleotide Sequence of GDF-1

To identify new members of the TGF-β superfamily that may be important for mouse embryogenesis, a cDNA library was constructed in lambda Zap II using poly A-selected RNA from whole embryos isolated at day 8.5 p.c. As indicated above, the library was screened with oligonucleotides selected on the basis of the predicted amino acid sequences of conversed regions among members of the superfamily. Among 600,000 recombinant phage screened, the oligonucleotide hybridized to 3 clones. Sequence analysis revealed that the 3 cDNA clones were likely to represent mRNA's derived from the same gene, which was designated GDF-1.

Northern analysis of day 8.5 embryonic RNA using the GDF-1 probe detected a single predominant mRNA species of approximately 1.4 kb in length. Because the original 3 cDNA isolates were all smaller than 1.4 kb, portions of the longest clone were used to re-screen the cDNA library to isolate a full-length clone. Hybridizing recombinant phage were seen at a frequency of approximately 1 per 200,000.

The entire nucleotide sequence of the longest cDNA clone obtained encoding GDF-1 is shown in FIG. 1. The 1387 bp sequence contains a single long open reading frame beginning with an initiating ATG at nucleotide 217 and potentially encoding a protein 357 amino acids with a molecular weight of 38,600. Upstream of the putative initiating ATG are two in-frame stop codons and no additional ATG's. Nucleotides 1259 to 1285 show a 25/27 match with the complement of the oligonucleotide selected from the original screening. The 3' end of the clone does not contain the canonical AAUAAA polyadenylation signal. Sequence analysis at the 3' end of 4 independent cDNA clones (all differing at their 5' ends) showed that 2 clones terminated at the same nucleotide, and the other 2 clones terminated at a site 7 nucleotides further downstream (these clones contained an additional AAAAATT sequence at the 3' end).

Two cDNA clones isolated during this screening process showed slight variations in their sequence from that shown in FIG. 1. In a limited segment from which the nucleotide sequence was determined, these 2 clones each showed 2 nucleotide changes, one resulting in a cysteine to serine substitution at amino acid 145 and the second representing a third position change that did not alter the amino acid sequence. These differences are unlikely to be cloning artifacts since they were found in independently-isolated clones. These changes may represent allelic differences or they may indicate the presence of multiple GDF-1 genes.

EXAMPLE 4

Combination use of GDF-1 and NT-3

Refolded *E. coli* derived rhGDF-1 (obtained as disclosed below) was tested for activity in a fiber outgrowth assay in chick sympathetic ganglion as described in Ebendal et al., 1995, *J. Neurosci. Res.* 40:276–284. Briefly, the assay was conducted as follows: An explanted sympathetic ganglion from a day 9 chicken embryo was explanted to a collagen gel and GDF-1 or NT-3 was applied. One day later the explant was scored on the basis of fiber outgrowth with a score of 0 indicating no outgrowth and a score of 5 indicating maximal outgrowth. Scores were recorded in a blinded fashion with two separate scores recorded by two individuals.

rhGD F-1 was added at various dilutions, but no change in outgrowth was seen in explants not exposed to NT-3.

However, when rhGDF-1 was added to explants previously exposed to 2 ng/ml NT-3, a robust potentiation of the neurite outgrowth promoting activity of NT-3 was seen. The data are summarized in Table 1 below. In Table 1 below, values represent mean scores for each culture as taken by two separate observers. A mean and standard deviation are set forth in Table 1 for each treatment.

The *E. coli* derived rhGDF-1 was obtained as follows. RhGDF-1 was produced in *E. coli* in inclusion bodies. The inclusion bodies were solubilized and reduced in 6M guanidine and 100 mM dithiothreitol. Reducing agent and denaturing agent was removed by reverse phase HPLC. The protein was dried down with a speed vac and resuspended in 8M urea and 5 mg/ml protein concentration. The protein solution was then diluted 1/100 in refolding buffer to a final concentration of 50 μg/ml. The refolding buffer contained 10 mM reduced glutathione, 1 mM oxidized glutathione and 50 mM tris buffer at pH 9.0. The protein was allowed to refold for 20 hours at 25° C. A sample of the refolded protein was then analyzed by reducing and non-reducing SDS-PAGE. The gel was stained by coomassie and the proportion of dimer was determined by densitometry. This dimer was found to be approximately 20% of the total protein. The refolded material was then frozen at −80° C. for storage.

TABLE 1

|  | Control | GDF-1 250 ng/ml | NT-3 2 ng/ml | NT3 + GDF-1 250 ng/ml | NT3 + GDF-1 25, 50 ng/ml | NT-3 + GDF-1 5, 10 ng/ml |
| --- | --- | --- | --- | --- | --- | --- |
|  | 0 | 0 | 1 | 2.1 | 3.2 | 1 |
|  | 0 | 0 | 2 | 3.5 | 2.8 | 2.5 |
|  | 0 | 0 | 1.5 | 4 | 3.8 | 3.6 |
|  | 0 |  | 2.5 | 2.5 | 3 | 1 |
|  | 0 |  | 1.4 | 3 | 1.5 | 1 |
|  | 0 |  | 2.3 | 3.3 | 1 |  |
|  |  |  | 1 | 3 | 0.8 |  |
|  |  |  | 2.8 | 3 | 2 |  |
| Mean StdDev | 0 | 0 | 1.69 | 3.05 | 2.26 | 1.82 |
|  | 0 | 0 | 0.74 | 0.58 | 1.10 | 1.19 |

EXAMPLE 5
GDF-1 Activity in Cerebellar Granule Cells

Administration of rhGDF-1 to cerebellar granule cells from rat significantly increased neuron cell number, BrdU incorporation, neurite outgrowth and cell clustering of the cells.

The invention has been described in detail with reference to preferred embodiments thereof. However, it will be appreciated that those skilled in the art, upon consideration of this disclosure, may make modifications and improvements within the spirit and scope of the invention.

What is claimed is:

1. A method of promoting neuronal fiber outgrowth or neuronal survival of cerebellar granule cells comprising administering to a mammal in need of promoting neuronal fiber outgrowth or neuronal survival of cerebellar granule cells suffering from or susceptible to nerve cell death or degeneration a therapeutically effective amount of GDF-1 (SEQ ID NO:2).

2. A method of claim 1, wherein the mammal has suffered brain or spinal cord trauma, brain or spinal cord ischemia, hypoxia or hypoglycemia.

3. A method of claim 1 or 2 wherein GDF-1 (SEQ ID NO:2) is administered after the mammal has suffered nerve cell death or degeneration.

4. A method of claim 1 or 2 wherein GDF-1 (SEQ ID NO:2) is administered to the mammal for at least two weeks after the mammal has suffered nerve cell death or degeneration.

5. The method of claim 1 or 2, wherein the administered GDF-1 is encoded by the nucleic acid of SEQ ID NO:1.

* * * * *

SEQUENCE LISTING

<160> NUMBER OF SEQ ID NOS: 4

<210> SEQ ID NO 1
<211> LENGTH: 1387
<212> TYPE: DNA
<213> ORGANISM: Mus sp.
<220> FEATURE:
<221> NAME/KEY: CDS
<222> LOCATION: (218)..(1288)

<400> SEQUENCE: 1

```
cccttctcca gggactctgg ctgccagcag ctccgccttt cagatcaatt ctcgaccacc         60
caccttggga ctgccgccca gtcctgccct ctggatcagt ggggtccaga cacgccccct        120
ccaggacctc aaagcacccc cgacctaagg tcaccagccc actggcccca gacgcagtgg        180
gctccgctga ctctcttgga cacctcctgg gaggaaa atg ctc cct gtc tgc cat        235
                                         Met Leu Pro Val Cys His
                                         1               5 cgt ttt tgc gac cac ctc ctc ctc ctg ctc ttg ctg ccc tcg acg acc        283
Arg Phe Cys Asp His Leu Leu Leu Leu Leu Leu Pro Ser Thr Thr
            10                  15                  20 ctg gcc ccc gcg cca gca tcc atg ggc ccc gct gcc gcc ctc ctc cag        331
Leu Ala Pro Ala Pro Ala Ser Met Gly Pro Ala Ala Ala Leu Leu Gln
                25                  30                  35 gtt ctt ggg ctt ccc gaa gcg ccc cgg agc gtc ccc aca cac cga cct        379
Val Leu Gly Leu Pro Glu Ala Pro Arg Ser Val Pro Thr His Arg Pro
        40                  45                  50
```

```
                                                                 -continued gtg cct cct gtc atg tgg cgc cta ttc cgt cgc cgt gac ccc cag gag        427
Val Pro Pro Val Met Trp Arg Leu Phe Arg Arg Arg Asp Pro Gln Glu
 55              60                  65                  70 gcc aga gtg gga cgc cct ctg cgg cca tgc cac gtg gag gaa cta ggg        475
Ala Arg Val Gly Arg Pro Leu Arg Pro Cys His Val Glu Glu Leu Gly
                 75                  80                  85 gtc gcc gga aac att gtg cgc cac atc ccc gac agc ggt ctg tcc tcc        523
Val Ala Gly Asn Ile Val Arg His Ile Pro Asp Ser Gly Leu Ser Ser
             90                  95                 100 agg ccc gca caa ccc gcc agg acc tcg ggg ctg tgc ccc gag tgg aca        571
Arg Pro Ala Gln Pro Ala Arg Thr Ser Gly Leu Cys Pro Glu Trp Thr
        105                 110                 115 gtc gtc ttt gac ctg tcg aat gtg gag ccc aca gag cgc cca aca cgc        619
Val Val Phe Asp Leu Ser Asn Val Glu Pro Thr Glu Arg Pro Thr Arg
120                 125                 130 gcg cgc tta gag ttg cgg ctg gag gct gag tgt gaa gat aca gga ggg        667
Ala Arg Leu Glu Leu Arg Leu Glu Ala Glu Cys Glu Asp Thr Gly Gly
135                 140                 145                 150 tgg gag cta agc gtg gca ctg tgg gcc gac gca gag cat cca ggg cct        715
Trp Glu Leu Ser Val Ala Leu Trp Ala Asp Ala Glu His Pro Gly Pro
                155                 160                 165 gag ctg ctg cgc gtg ccg gcg cca cca ggg gtg ctc ctg cgc gca gac        763
Glu Leu Leu Arg Val Pro Ala Pro Pro Gly Val Leu Leu Arg Ala Asp
            170                 175                 180 cta ctg ggg act gca gta gcc gcc aac gca tca gtg ccc tgt act gtg        811
Leu Leu Gly Thr Ala Val Ala Ala Asn Ala Ser Val Pro Cys Thr Val
        185                 190                 195 cgc ctg gcg ctg tca ctg cac cct ggg gcc act gca gcc tgt ggg cgc        859
Arg Leu Ala Leu Ser Leu His Pro Gly Ala Thr Ala Ala Cys Gly Arg
    200                 205                 210 ctg gct gag gcc tcc ctg ctg ctg gtg acg ctg gac cca cgc ctg tgt        907
Leu Ala Glu Ala Ser Leu Leu Leu Val Thr Leu Asp Pro Arg Leu Cys
215                 220                 225                 230 ccc ttg ccg cga ttg cgg cgc cac acg gag ccc agg gta gaa gtt ggt        955
Pro Leu Pro Arg Leu Arg Arg His Thr Glu Pro Arg Val Glu Val Gly
                235                 240                 245 cca gtg ggc act tgt cgt acc cga cgg ttg cat gtg agc ttc cgt gag       1003
Pro Val Gly Thr Cys Arg Thr Arg Arg Leu His Val Ser Phe Arg Glu
            250                 255                 260 gtg ggc tgg cac cgt tgg gtg atc gcg ccg cgt ggc ttc cta gcc aac       1051
Val Gly Trp His Arg Trp Val Ile Ala Pro Arg Gly Phe Leu Ala Asn
        265                 270                 275 ttc tgc cag ggc acg tgc gca cta ccc gaa acg ctg agg gga ccc ggc       1099
Phe Cys Gln Gly Thr Cys Ala Leu Pro Glu Thr Leu Arg Gly Pro Gly
    280                 285                 290 ggg ccg cct gca ctc aac cac gct gtg ctg cgc gcg ctc atg cac gca       1147
Gly Pro Pro Ala Leu Asn His Ala Val Leu Arg Ala Leu Met His Ala
295                 300                 305                 310 gct gct ccc acc ccg ggt gca ggc tcg ccc tgc tgc gtg cca gag cgt       1195
Ala Ala Pro Thr Pro Gly Ala Gly Ser Pro Cys Cys Val Pro Glu Arg
                315                 320                 325 cta tca ccc atc tcc gtg ctc ttc ttc gac aat agt gac aac gtg gtc       1243
Leu Ser Pro Ile Ser Val Leu Phe Phe Asp Asn Ser Asp Asn Val Val
            330                 335                 340 ctg cga cac tac gaa gac atg gtg gtg gat gag tgt ggc tgc cgt           1288
Leu Arg His Tyr Glu Asp Met Val Val Asp Glu Cys Gly Cys Arg
        345                 350                 355 tgaccacccg ggacccctt tcagggaccg ccccacgcaa aagcaggac tgtttgttca       1348 tgtttattg gtgacaaaaa gcttaaaaca aatttgact                             1387
```

```
<210> SEQ ID NO 2
<211> LENGTH: 357
<212> TYPE: PRT
<213> ORGANISM: Mus sp.

<400> SEQUENCE: 2

Met Leu Pro Val Cys His Arg Phe Cys Asp His Leu Leu Leu Leu
 1               5                  10                  15

Leu Leu Pro Ser Thr Thr Leu Ala Pro Ala Pro Ala Ser Met Gly Pro
                 20                  25                  30

Ala Ala Ala Leu Leu Gln Val Leu Gly Leu Pro Glu Ala Pro Arg Ser
             35                  40                  45

Val Pro Thr His Arg Pro Val Pro Pro Val Met Trp Arg Leu Phe Arg
     50                  55                  60

Arg Arg Asp Pro Gln Glu Ala Arg Val Gly Arg Pro Leu Arg Pro Cys
 65                  70                  75                  80

His Val Glu Glu Leu Gly Val Ala Gly Asn Ile Val Arg His Ile Pro
                 85                  90                  95

Asp Ser Gly Leu Ser Ser Arg Pro Ala Gln Pro Ala Arg Thr Ser Gly
            100                 105                 110

Leu Cys Pro Glu Trp Thr Val Val Phe Asp Leu Ser Asn Val Glu Pro
            115                 120                 125

Thr Glu Arg Pro Thr Arg Ala Arg Leu Glu Leu Arg Leu Glu Ala Glu
            130                 135                 140

Cys Glu Asp Thr Gly Gly Trp Glu Leu Ser Val Ala Leu Trp Ala Asp
145                 150                 155                 160

Ala Glu His Pro Gly Pro Glu Leu Leu Arg Val Pro Ala Pro Pro Gly
                165                 170                 175

Val Leu Leu Arg Ala Asp Leu Leu Gly Thr Ala Val Ala Ala Asn Ala
                180                 185                 190

Ser Val Pro Cys Thr Val Arg Leu Ala Leu Ser Leu His Pro Gly Ala
            195                 200                 205

Thr Ala Ala Cys Gly Arg Leu Ala Glu Ala Ser Leu Leu Leu Val Thr
            210                 215                 220

Leu Asp Pro Arg Leu Cys Pro Leu Pro Arg Leu Arg Arg His Thr Glu
225                 230                 235                 240

Pro Arg Val Glu Val Gly Pro Val Gly Thr Cys Arg Thr Arg Arg Leu
                245                 250                 255

His Val Ser Phe Arg Glu Val Gly Trp His Arg Trp Val Ile Ala Pro
            260                 265                 270

Arg Gly Phe Leu Ala Asn Phe Cys Gln Gly Thr Cys Ala Leu Pro Glu
            275                 280                 285

Thr Leu Arg Gly Pro Gly Pro Pro Ala Leu Asn His Ala Val Leu
            290                 295                 300

Arg Ala Leu Met His Ala Ala Pro Thr Pro Gly Ala Gly Ser Pro
305                 310                 315                 320

Cys Cys Val Pro Glu Arg Leu Ser Pro Ile Ser Val Leu Phe Phe Asp
                325                 330                 335

Asn Ser Asp Asn Val Val Leu Arg His Tyr Glu Asp Met Val Val Asp
            340                 345                 350

Glu Cys Gly Cys Arg
            355
```

```
-continued

<210> SEQ ID NO 3
<211> LENGTH: 27
<212> TYPE: DNA
<213> ORGANISM: Mus sp.

<400> SEQUENCE: 3
gcagccacac tcctccacca ccatgtt                                       27

<210> SEQ ID NO 4
<211> LENGTH: 9
<212> TYPE: PRT
<213> ORGANISM: Mus sp.

<400> SEQUENCE: 4

Asn Met Val Val Glu Glu Cys Gly Cys
 1               5
```